United States Patent
Chen et al.

(10) Patent No.: US 11,441,163 B2
(45) Date of Patent: Sep. 13, 2022

(54) ENZYME-CATALYZED SYNTHESIS OF (1S,5R)-BICYCLOLACTONE

(71) Applicant: Fudan University, Shanghai (CN)

(72) Inventors: Fener Chen, Shanghai (CN); Kejie Zhu, Shanghai (CN); Zedu Huang, Shanghai (CN); Dang Cheng, Shanghai (CN); Jiaqi Wang, Shanghai (CN); Yuan Tao, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 17/038,081

(22) Filed: Sep. 30, 2020

(65) Prior Publication Data
US 2021/0355516 A1 Nov. 18, 2021

(30) Foreign Application Priority Data

May 14, 2020 (CN) .......................... 202010409629.7

(51) Int. Cl.
| | | |
|---|---|---|
| C12P 17/04 | (2006.01) | |
| C12N 1/20 | (2006.01) | |
| C12N 9/02 | (2006.01) | |
| C12N 15/70 | (2006.01) | |

(52) U.S. Cl.
CPC ................ *C12P 17/04* (2013.01); *C12N 1/20* (2013.01); *C12N 9/0073* (2013.01); *C12N 15/70* (2013.01)

(58) Field of Classification Search
None
See application file for complete search history.

(56) References Cited

FOREIGN PATENT DOCUMENTS

CN 108084129 A 5/2018

OTHER PUBLICATIONS

Vgronique A., Alain A., Roland F.; Microbial Transformations 16. One-step synthesis of a pivotal prostaglandin chiral synthon via a highly enantioselective microbiological Baeyer-Villiger type reaction; Tetrahedron Lett., 1989, 30, 3663.

Véronique A., Roland F; Microbiological Transformations. 22. Microbiologically Mediated Baeyer-Villiger Reactions: A Unique Route to Several Bicyclic 7-Lactones in High Enantiomeric Purity;J. Org. Chem., 1992, 57, 1306.

Masaji O., Masami O.;Chiral synthons by Ester Hydrolysis Catalyzed by Pig Liver Esterase;Organic Reactions, 1989, 37,24-25).

Tsutomu S., Kunio O.; An Expedient Route to (-)-cis-2-Oxabicyclo[3.3.0]oct-6-en-3-one via a meso-Asymmetrization; Synlett, 1996, 319.

Carsten B., Oliver B.; Zirconium-Mediated Asymmetric Baeyer-Villiger Oxidation;Chirality, 2000, 12, 523.

Michael P. D., Arthur J. C.; A short stereoselective synthesis of (+)- and (-)-2-oxabicyclo[3.3.0]oct-6-en-3-one by intramolecular carbon-hydrogen insertion catalyzed by chiral dirhodium(II) carboxamidates;Tetrahedron: Asymmetry, 2003, 14, 925.

Akira W., Tatsuya U., et al.; Zr[bis(salicylidene)ethylenediaminato]-mediated Baeyer-Villiger oxidation: Stereospecific synthesis of abnormal and normal lactones;Proc. Natl. Acad. Sci. 2004, 101, 5737-5742.

Senmiao X., Zheng W., et al. ;Asymmetric Baeyer-Villiger Oxidation of 2,3- and 2,3,4-Substituted Cyclobutanones Catalyzed by Chiral Phosphoric Acids with Aqueous H2O2 as the Oxidant;Eur. J. Org. Chem.,2011,110.

*Primary Examiner* — Iqbal H Chowdhury (57) ABSTRACT

An enzyme-catalyzed synthesis of (1S,5R)-bicyclolactone. A first genetically-engineered bacterium containing Baeyer-Villiger monooxygenase gene and a second genetically-engineered bacterium containing glucose dehydrogenase gene are constructed and then suspended with culture medium to prepare a first suspension and a second suspension, respectively. The first and second suspensions are centrifuged to respectively produce a first supernatant containing Baeyer-Villiger monooxygenase and a second supernatant containing glucose dehydrogenase, which are mixed. The mixed supernatant is then mixed with a raceme of a substituted bicyclo[3.2.0]-hept-2-en-6-one, a solvent, a hydrogen donor and a cofactor to perform an asymmetric Baeyer-Villiger oxidation to produce the (1S,5R)-bicyclolactone, where an amino acid sequence of the Baeyer-Villiger monooxygenase is shown in SEQ ID NO:1.

20 Claims, 9 Drawing Sheets

Specification includes a Sequence Listing.

SEQUENCE LISTING

<160> NUMBER OF SEQ ID NOS: 3

<210> SEQ ID NO 1
<211> LENGTH: 541
<212> TYPE: PRT
<213> ORGANISM: Artificial Sequence
<220> FEATURE:
<223> OTHER INFORMATION: synthetic

<400> SEQUENCE: 1

```
Met Thr Ala Gln Ile Ser Pro Thr Val Val Asp Ala Val Val Ile Gly
1               5                   10                  15

Ala Gly Phe Gly Gly Ile Tyr Ala Val His Lys Leu His Asn Glu Gln
            20                  25                  30

Gly Leu Thr Val Val Gly Phe Asp Lys Ala Asp Gly Pro Gly Gly Thr
        35                  40                  45

Trp Tyr Trp Asn Arg Tyr Pro Gly Ala Leu Ser Asp Thr Glu Ser His
50                  55                  60

Leu Tyr Arg Phe Ser Phe Asp Arg Asp Leu Leu Gln Asp Gly Thr Trp
65                  70                  75                  80

Lys Thr Thr Tyr Ile Thr Gln Pro Glu Ile Leu Glu Tyr Leu Glu Ser
                85                  90                  95

Val Val Asp Arg Phe Asp Leu Arg Arg His Phe Arg Phe Gly Thr Glu
            100                 105                 110

Val Thr Ser Ala Ile Tyr Leu Glu Asp Glu Asn Leu Trp Glu Val Ser
        115                 120                 125

Thr Asp Lys Gly Glu Val Tyr Arg Ala Lys Tyr Val Val Asn Ala Val
130                 135                 140

Gly Leu Leu Ser Ala Ile Asn Phe Pro Asp Leu Pro Gly Leu Asp Thr
145                 150                 155                 160

Phe Glu Gly Glu Thr Ile His Thr Ala Ala Trp Pro Glu Gly Lys Asn
                165                 170                 175

Leu Ala Gly Lys Arg Val Gly Val Ile Gly Thr Gly Ser Thr Gly Gln
            180                 185                 190

Gln Val Ile Thr Ala Leu Ala Pro Glu Val Glu His Leu Thr Val Phe
        195                 200                 205

Val Arg Thr Pro Gln Tyr Ser Val Pro Val Gly Asn Arg Pro Val Thr
210                 215                 220

Lys Glu Gln Ile Asp Ala Ile Lys Ala Asp Tyr Asp Gly Ile Trp Asp
225                 230                 235                 240

Ser Val Lys Lys Ser Ala Val Ala Phe Gly Phe Glu Glu Ser Thr Leu
                245                 250                 255

Pro Ala Met Ser Val Ser Glu Glu Arg Asn Arg Ile Phe Gln Glu
            260                 265                 270

Ala Trp Asp His Gly Gly Phe Arg Phe Met Phe Gly Thr Phe Gly
            275                 280                 285

Asp Ile Ala Thr Asp Glu Ala Ala Asn Glu Ala Ala Ser Phe Ile
            290                 295                 300

Arg Ser Lys Ile Ala Glu Ile Ile Glu Asp Pro Glu Thr Ala Arg Lys
305                 310                 315                 320

Leu Met Pro Thr Gly Leu Tyr Ala Lys Arg Pro Leu Cys Asp Asn Gly
                325                 330                 335

Tyr Tyr Glu Val Tyr Asn Arg Pro Asn Val Gly Ala Val Ala Ile Lys
            340                 345                 350

Glu Asn Pro Ile Arg Glu Val Thr Ala Lys Gly Val Val Thr Glu Asp
        355                 360                 365

Gly Val Leu His Glu Leu Asp Val Leu Val Phe Ala Thr Gly Phe Asp
        370                 375                 380

Ala Val Asp Gly Asn Tyr Arg Arg Ile Glu Ile Arg Gly Arg Asn Gly
385                 390                 395                 400

Leu His Ile Asn Asp His Trp Asp Gly Gln Pro Thr Ser Tyr Leu Gly
```

```
                405                 410                 415
Val Thr Thr Ala Asn Phe Pro Asn Trp Phe Met Val Leu Gly Pro Asn
                420                 425                 430

Gly Pro Phe Thr Asn Leu Pro Pro Ser Ile Glu Thr Gln Val Glu Trp
            435                 440                 445

Ile Ser Asp Thr Val Ala Tyr Ala Glu Arg Asn Glu Ile Arg Ala Ile
        450                 455                 460

Glu Pro Thr Pro Glu Ala Glu Glu Trp Thr Gln Thr Cys Thr Asp
465                 470                 475                 480

Ile Ala Asn Ala Thr Leu Phe Thr Arg Gly Asp Ser Trp Ile Phe Gly
                485                 490                 495

Ala Asn Val Pro Gly Lys Lys Pro Ser Val Leu Phe Tyr Leu Gly Gly
            500                 505                 510

Leu Gly Asn Tyr Arg Asn Val Leu Ala Gly Val Val Ala Asp Ser Tyr
        515                 520                 525

Arg Gly Phe Glu Leu Lys Ser Ala Val Pro Val Thr Ala
    530                 535                 540
```

<210> SEQ ID NO 2
<211> LENGTH: 1626
<212> TYPE: DNA
<213> ORGANISM: Rhodococcus sp.

<400> SEQUENCE: 2

```
atgacggcgc agattagccc gaccgtggtg gacgcggttg ttattggtgc cggcttcggc    60
ggcatttacg cggtgcacaa gctgcacaac gaacaaggtc tgaccgttgt gggctttgat   120
aaggccgatg gcccgggcgg tacgtggtat tggaatcgct atccgggcgc gctgagcgac   180
acggaaagtc atctgtaccg ctttagcttc gatcgcgatc tgctccaaga tggtacgtgg   240
aagacgacct acatcacgca gccggagatt ctggagtatc tggagagcgt ggttgatcgc   300
ttcgatctgc gccgccattt ccgcttcggc accgaggtga cgagcgcgat ttatctggaa   360
gatgagaatc tgtgggaagt gagcaccgac aaaggtgagg tttaccgcgc caagtacgtt   420
gtgaatgccg ttggtctgct gagtgccatt aacttcccgg atctgccggg cctcgatacc   480
ttcgaaggcg agaccatcca tacggccgcg tggccagaag gcaaaaacct cgccggcaaa   540
cgcgtgggtg tgatcggtac cggcagcacc ggtcagcaag ttattacggc gctggcgcca   600
gaggtggaac atctgacggt tttcgttcgc accccgcagt atagcgttcc agttggcaac   660
cgtccagtga ccaaggagca gatcgatgcg atcaaagccg actacgacgg catctgggac   720
agtgtgaaaa agagcgcggt tgcctttggc ttcgaagaaa gcacgctccc ggccatgagc   780
gtgagcgaag aagagcgcaa ccgcattttc aagaagcgt gggatcatgg tggtggcttc   840
cgctttatgt tcggcacctt tggcgacatc gccacggatg aggccgcgaa tgaagcggcg   900
gcgagcttca tccgcagcaa aatcgccgag atcatcgaag cccagagac ggcgcgcaag   960
ctgatgccaa ccggcctcta cgccaaacgc ccactgtgcg acaatggcta ctacgaggtg  1020
tacaatcgcc caaacgtgga agccgtggcc attaaggaaa acccgatccg cgaagtgacc  1080
gccaaaggcg ttgttacgga agatggtgtg ctgcacgaac tggatgtgct ggttttgcg  1140
accggctttg atgccgtgga tggcaattac cgccgcattg agatccgtgg ccgcaatggc  1200
ctccatatca acgatcactg ggacggtcag ccgaccagct atctcggtgt taccaccgcg  1260
aacttcccga attggttcat ggtgctgggc caaatggtc catttaccaa tctgccgccg  1320
agcatcgaga cccaagtgga atggattagc gataccgtgg cctatgcgga acgtaacgag  1380
```

-continued

```
atccgcgcga tcgaaccaac gccggaagcc gaggaggaat ggacccagac gtgcaccgat    1440
attgcgaacg ccacgctgtt tacccgcggc gatagctgga tttttggtgc caacgttccg    1500
ggtaagaagc caagtgtgct cttctacctc ggcggtctgg gtaattatcg caatgtgctg    1560
gcgggtgtgg tggccgatag ctatcgcggc ttcgaactga aaagcgccgt tccggttacg    1620
gcgtaa                                                               1626

<210> SEQ ID NO 3
<211> LENGTH: 1089
<212> TYPE: DNA
<213> ORGANISM: Thermoplasma acidophilum

<400> SEQUENCE: 3
atggcaactg aacagaaagc cattgtgaca gatgcgccca aggtggcgt gaaatacaca      60 acaatagaca tgcctgaacc ggaacattac gacgccaagc tttcacctgt atacatagga    120
atatgcggaa cggatcgtgg agaggtggct ggtgccctgt cattcacgta caatccagag    180
ggggagaatt ttcttgttct cgggcacgag gcgcttctgc gtgttgacga tgcccgtgat    240
aatggctaca taaagaaggg cgatcttgta gtaccccctcg tgagaaggcc tggaaaatgc    300
atcaactgca gaataggcag gcaggataac tgttccatag gtgatccgga caaacatgag    360
gctggaataa ctgggcttca tggtttcatg cgcgatgtca tatacgacga tatagagtat    420
ctcgttaagg ttgaagatcc agaactggga aggatcgcag tgcttacgga gcctctgaaa    480
aatgtcatga aggcttttga ggtcttcgac gttgtgtcaa aaagatccat attcttcggg    540
gacgattcca cgctcatagg taagaggatg gtcataatag gcagcgggag cgaggctttc    600
ctctactcgt ttgcaggcgt agatcgcggt ttcgacgtca caatggtgaa caggcacgat    660
gagacggaaa acaagctgaa gatcatggac gagttcggcg tcaagttcgc aaactaccgtt    720 aaggacatgc cggaaaagat agatctcctg gttgacacca gtggtgatcc aacgacgaca    780
ttcaagttcc tcaggaaggt aaacaacaac ggcgtcgtca tattgttcgg cacgaacggc    840
aaggcgcccg gctatccagt ggatggcgag gacatagatt acatcgtgga gaggaacata    900
acaatagccg gatcggttga tgccgcgaag atacactacg tgcaggccct tcagtccctc    960
agcaactgga acagaagaca cccagatgcc atgaagagca tcataacata cgaggcgaag   1020
ccgtccgaaa ccaacatatt cttccagaaa ccacacggag agataaagac ggtgataaag   1080
tggcagtga                                                           1089
```

ENZYME-CATALYZED SYNTHESIS OF (1S,5R)-BICYCLOLACTONE

REFERENCE TO AN ELECTRONIC SEQUENCE LISTING

The contents of the electronic sequence listing (Sequence-Listing-2020-12-09.TXT; Size: 9,000 bytes; and Date of Creation: Dec. 9, 2020) is herein incorporated by reference in its entirety.

CROSS-REFERENCE TO RELATED APPLICATIONS

This application claims the benefit of priority from Chinese Patent Application No. 202010409629.7, filed on May 14, 2020. The content of the aforementioned applications, including any intervening amendments thereto, is incorporated herein by reference in its entirety.

TECHNICAL FIELD

The present application relates to biopharmaceutics, and more particularly to a method of enzymatically synthesizing (1S,5R)-bicyclolactone.

BACKGROUND (1S,5R)-bicyclolactone of formula (I) is a key intermediate in the synthesis of prostaglandin.

(I)

In the formula (I), R is hydrogen, fluorine, chlorine, bromine, iodine, $C_1$-$C_8$ alkyl or cycloalkyl, phenyl, mono-substituted or polysubstituted aryl or aralkyl, thienyl, furyl, naphthyl or pyridyl; and n is 1-10.

Veronique et al. (Veronique A., Alain A., Roland F., Microbial Transformations 16. One-step synthesis of a pivotal prostaglandin chiral synthon via a highly enantioselective microbiological Baeyer-Villiger type reaction[J]. *Tetrahedron Lett.*, 1989, 30, 3663) employed bicyclo[3.2.0]-hept-2-en-6-one as a starting material to construct the (1S,5R)-bicyclolactone (I) by one step through microbiologically promoted enantioselective Baeyer-Villiger oxidation. Furstuss et al. (Véronique A., Roland F. Microbiological Transformations. 22. Microbiologically Mediated Baeyer-Villiger Reactions: A Unique Route to Several Bicyclic 7-Lactones in High Enantiomeric Purity[J]. *J. Org. Chem.*, 1992, 57, 1306) employed microbiologically mediated enantioselective Baeyer-Villiger oxidation to produce the lactone with high enantioselectivity (>95% ee), but there were also undesired lactone products produced with high enantioselectivity, which were difficult to be removed since they were similar to target products in polarity.

Masami et al. disclosed a method for preparing the (1S,5R)-bicyclolactone (I) by stereoselectively hydrolyzing a meso-diester under the catalysis of pig liver esterase (Masaji O., Masami O., Chiral synthons by Ester Hydrolysis Catalyzed by Pig Liver Esterase[J]. *Organic Reactions*, 1989, 37, 24-25). Ogasawara et al. (Tsutomu S., Kunio O., An Expedient Route to (−)-cis-2-Oxabicyclo[3.3.0]oct-6-en-3-one via a meso-Asymmetrization[J]. *Synlett*, 1996, 319) reported a method of constructing the (1S,5R)-bicyclolactone (I) through lipase-catalyzed desymmetrization. However, these methods are merely suitable for small-scale production and have troublesome post-processing.

It has been first reported by Bolm et al. (Carsten B., Oliver B., Zirconium-Mediated Asymmetric Baeyer-Villiger Oxidation[J]. *Chirality*, 2000, 12, 523) in 2000 that a zirconium-chiral binaphthol catalyst can be applied to the asymmetrical Baeyer-Villiger oxidation to produce (1S,5R)-lactone with 35% ee. Doyle et al. (Michael P. D., Arthur J. C., A short stereoselective synthesis of (+)- and (−)-2-oxabicyclo[3.3.0] oct-6-en-3-one by intramolecular carbon-hydrogen insertion catalyzed by chiral dirhodium(II) carboxamidates[J]. *Tetrahedron: Asymmetry*, 2003, 14, 925) can produce the (1S,5R)-lactone with 73% yield and 93% ee by means of chiral dirhodium(II)-catalyzed asymmetric C—H insertion. Katsuki et al. (Akira W., Tatsuya U., et al. Zr[bis(salicylidene) ethylenediaminato]-mediated Baeyer-Villiger oxidation: Stereospecific synthesis of abnormal and normal lactones[J]. *Proc. Natl. Acad. Sci.* 2004, 101, 5737-5742) proposed a chiral Zr-Salen-mediated asymmetric Baeyer-Villiger oxidation, by which (1S,5R)-lactone with 23% yield and 91% ee as well as abnormal lactone with 38% yield were produced. Ding Kuiling et al. (Senmiao X., Zheng W., et al. Asymmetric Baeyer-Villiger Oxidation of 2,3- and 2,3,4-Substituted Cyclobutanones Catalyzed by Chiral Phosphoric Acids with Aqueous $H_2O_2$ as the Oxidant[J]. *Eur. J. Org. Chem.*, 2011, 110) also reported the use of a chiral binaphthyl phosphonic acid to asymmetrically catalyze the Baeyer-Villiger oxidation to construct the (1S,5R)-lactone with 64% yield and 32% ee. Unfortunately, the above methods all have the disadvantages of expensive catalyst, insufficient catalytic efficiency and low enantioselectivity, and thus they are not suitable for the industrial application.

SUMMARY

An object of the present invention is to provide a method of synthesizing (1S,5R)-bicyclolactone, which has high product purity and simple operation, and makes for easy purification, to overcome the defects in the prior microbiologically-mediated synthesis of (1S,5R)-bicyclolactones.

Technical solutions of the invention are specifically described as follows.

The present invention provides a method of synthesizing a (1S,5R)-bicyclolactone, comprising:

(1) constructing a first genetically-engineered bacterium containing a Baeyer-Villiger monooxygenase gene and a second genetically-engineered bacterium containing a glucose dehydrogenase gene;

(2) preparing a first suspension of resting cells of the first genetically-engineered bacterium and a second suspension of resting cells of the second genetically-engineered bacterium;

(3) preparing a first supernatant containing Baeyer-Villiger monooxygenase and a second supernatant containing glucose dehydrogenase; and (4) mixing the first supernatant and the second supernatant; mixing the mixed supernatant with a raceme of a substituted bicyclo[3.2.0]-hept-2-en-6-one, a solvent, a hydrogen donor and a cofactor to perform an asymmetric Baeyer-Villiger oxidation to produce the (1S,5R)-bicyclolactone;

wherein the Baeyer-Villiger monooxygenase has an amino acid sequence as shown in SEQ ID NO:1, or an amino acid sequence having an identity of more than 80% to SEQ ID NO:1.

In some embodiments, a sequence of the Baeyer-Villiger monooxygenase gene is shown in SEQ ID NO:2, and a sequence of the glucose dehydrogenase gene is shown in SEQ ID NO:3.

In some embodiments, the first genetically-engineered bacterium and the second genetically-engineered bacterium are both constructed from *Escherichia coli* BL21 (DE3) containing an expression vector pET-28a.

In some embodiments, wherein the first suspension is prepared through steps of:

inoculating the first genetically-engineered bacterium to a first kanamycin-containing medium followed by activation on a shaker;

culturing the first genetically-engineered bacterium to an optical density $OD_{600}$ of 0.8-1.2, and adding a first inducer followed by continuous culture;

centrifuging a culture system of the first genetically-engineered bacterium, and collecting cells of the first genetically-engineered bacterium; and suspending the cells of the first genetically-engineered bacterium with a first buffered solution to prepare the first suspension; and the second suspension is prepared through steps of:

inoculating the second genetically-engineered bacterium to a second kanamycin-containing medium followed by activation on the shaker;

culturing the second genetically-engineered bacterium to an optical density $OD_{600}$ of 0.8-1.2, and adding a second inducer followed by continuous culture;

centrifuging a culture system of the second genetically-engineered bacterium, and collecting cells of the second genetically-engineered bacterium; and suspending the cells of the second genetically-engineered bacterium with a second buffered solution to prepare the second suspension.

In some embodiments, the first inducer and the second inducer are both 0.05-0.8 mM isopropylthiogalactoside (IPTG); after the first inducer is added, the culture is performed at 15-25° C. for 8-24 h; and after the second inducer is added, the culture is performed at 15-25° C. for 8-24 h.

In some embodiments, the first buffered solution and the second buffered solution are both a 30-300 mM sodium phosphate buffered solution.

In some embodiments, wherein the first supernatant is prepared by sequentially ultrasonicating and centrifuging the first suspension; and the second supernatant is prepared by sequentially ultrasonicating and centrifuging the second suspension.

In some embodiments, in step (4), a volume ratio of the first supernatant to the second supernatant is 3.5-29:1.

In some embodiments, the volume ratio of the first supernatant to the second supernatant is 20-29:1.

In some embodiments, the reaction mixture of the asymmetric Baeyer-Villiger oxidation comprises 1.0-100 g/L of the raceme of the substituted bicyclo [3.2.0]-hept-2-en-6-one; 5-750 g/L of the hydrogen donor and 0-0.5 mM of the cofactor; a cell concentration of the first suspension is 0.1-25 g (wet weight)/L; and a cell concentration of the second suspension is 0.1-25 g (wet weight)/L.

In some embodiments, the hydrogen donor is glucose, and the cofactor is a combination of $NADP^+/NADPH$ and $FADH_2/FAD$.

In some embodiments, the asymmetric Baeyer-Villiger oxidation is performed at 20-40° C. and pH 6.0-8.0.

In some embodiments, the asymmetric Baeyer-Villiger oxidation is performed at 20-25° C. and pH 6.5-7.5.

In some embodiments, in the asymmetric Baeyer-Villiger oxidation, the solvent is selected from the group consisting of dimethyl sulfoxide, N,N-dimethylformamide, N,N-dimethylacetamide, benzene, toluene, ethylbenzene, chlorobenzene, bromobenzene, n-hexane, cyclohexane, acetonitrile, ethyl acetate, dichloromethane, 1,2-dichloroethane, methanol, ethanol, isopropanol and a combination thereof.

In some embodiments, the solvent is a mixture of toluene, 1,2-dichloroethane and a phosphate buffered solution.

In some embodiments, in the solvent, a volume ratio of the toluene to the 1,2-dichloroethane to the phosphate buffered solution is 3:2:95.

In some embodiments, the phosphate buffered solution is a 100-250 mM phosphate buffered solution at pH 6.5-7.5.

In some embodiments, the method further comprises:

after the asymmetric Baeyer-Villiger oxidation is completed, subjecting the reaction mixture to extraction with ethyl acetate, and collecting organic phases;

combining the organic phases;

washing the combined organic phase with a saturated sodium bicarbonate solution, water and a saturated sodium chloride solution in sequence; and drying the washed organic phase with anhydrous sodium sulfate followed by vacuum distillation to produce the (1S,5R)-bicyclolactone.

In some embodiments, the extraction is performed 3-4 times with an equal volume of ethyl acetate; and the washing is performed twice with the saturated sodium bicarbonate solution, once with water and once with the saturated sodium chloride solution.

The asymmetric Baeyer-Villiger oxidation is shown in the following scheme:

In the asymmetric Baeyer-Villiger oxidation shown in the above scheme, on one hand, the Baeyer-Villiger monooxygenase CHMO (cyclohexanone monooxygenase) expressed by the first genetically-engineered bacterium regioselectively catalyzes the asymmetric oxidation of the raceme of the substituted bicyclo[3.2.0]-hept-2-en-6-one (II) to produce the (1S,5R)-bicyclolactone (I), and at the same time, the reduced cofactor $FADH_2$ is converted into the oxidized cofactor FAD; on the other hand, the glucose dehydrogenase expressed by the second genetically-engineered bacterium oxidizes glucose to gluconolactone, accompanied by the consumption of the oxidized coenzyme factor $NADP^+$ and the regeneration of the reduced coenzyme factor NADPH. Meanwhile, the reduced coenzyme factor NADPH reduces the oxidized cofactor FAD to the reduced cofactor $FADH_2$, and the reduced coenzyme factor NADPH itself is accordingly converted to the oxidized coenzyme factor $NADP^+$, forming a cycle of the consumption and regeneration of the two coenzyme factors to drive the main reaction.

Compared to the prior art, the invention has the following beneficial effects.

(1) The invention provides a new method for biologically synthesizing (1S,5R)-bicyclolactone (I), in which a genetically-engineered bacterium expressing CHMO and a genetically-engineered bacterium expressing glucose dehydrogenase GDH are employed to catalyze the asymmetric oxidation of the raceme of the substituted bicyclo[3.2.0]-hept-2-en-6-one (II) to produce the (1S,5R)-bicyclolactone (I).

(2) The invention reaches a balance between the consumption and the regeneration of coenzymes during the reaction through the combination of the CHMO and the glucose dehydrogenase. Moreover, due to the self-isomerization effect of the regioisomers, the desired product is greatly different from other undesired products in the polarity, which is conducive to the purification of the desired product, optimizing the synthesis of the (1S,5R)-bicyclolactone (I).

(3) The readily-available Baeyer-Villiger monooxygenase CHMO is used herein as catalyst, allowing for reduced production cost.

(4) The genetically-engineered bacterial strains used herein are readily available, and the product has high enantioselectivity, and is easy to separate.

DETAILED DESCRIPTION OF EMBODIMENTS

The invention will be described in detail below in conjunction with the embodiments and drawings to make the content, features, objects and advantages of the technical solutions of the invention clearer. The embodiments are merely illustrative of the present invention, and are not intended to limit the invention.

Unless otherwise specified, the materials and reagents used in the following examples are all commercially available.

Example 1 Construction of Genetically-engineered Bacteria and Induced Expression of CHMO-Rhodo1 and GDH Genes 1. Construction of CHMO Genetically-Engineered Bacteria and Induced Expression of CHMO-Rhodo1 Gene (1) Construction of recombinant expression vector The CHMO-Rhodo1 gene (as shown in SEQ ID NO:2) was cloned into a vector pET-28a which was digested with two restriction enzymes NdeI and XhoI in advance to construct a recombinant expression vector (i.e., the pET-28a plasmid carrying the CHMO-Rhodo1 gene) named pET-28a/CHMO-Rhodo1.

The gene of Baeyer-Villiger monooxygenase CHMO-Rhodo1 had a nucleotide sequence as shown in SEQ ID NO: 2, which was derived from *Rhodococcus* sp.

(2) Preparation of CHMO genetically-engineered bacteria

The recombinant expression vector pET-28a/CHMO-Rhodo1 was transformed into *Escherichia coli* BL21(DE3) competent cells, which was specifically described as follows.

50 ng of the recombinant expression vector pET-28a/CHMO-Rhodo1 was added into 50 μL of the competent cells. The cells were shaken slightly, placed on ice for 30 min and subjected to heat shock at 42° C. for 45 seconds. Then 700 μL of a culture medium was added, and the cells were recovered in a constant temperature incubation shaker for 50 min (37° C., 200 rpm), and spread onto a kanamycin-containing solid Luria-Bertani (LB) medium. The solid LB medium was incubated in a constant temperature incubator at 37° C. for 16 h to obtain the CHMO genetically-engineered bacteria, which were named BL21(DE3)-CHMO-Rhodo1.

(3) Preparation of CHMO-containing supernatant

Figure 1:
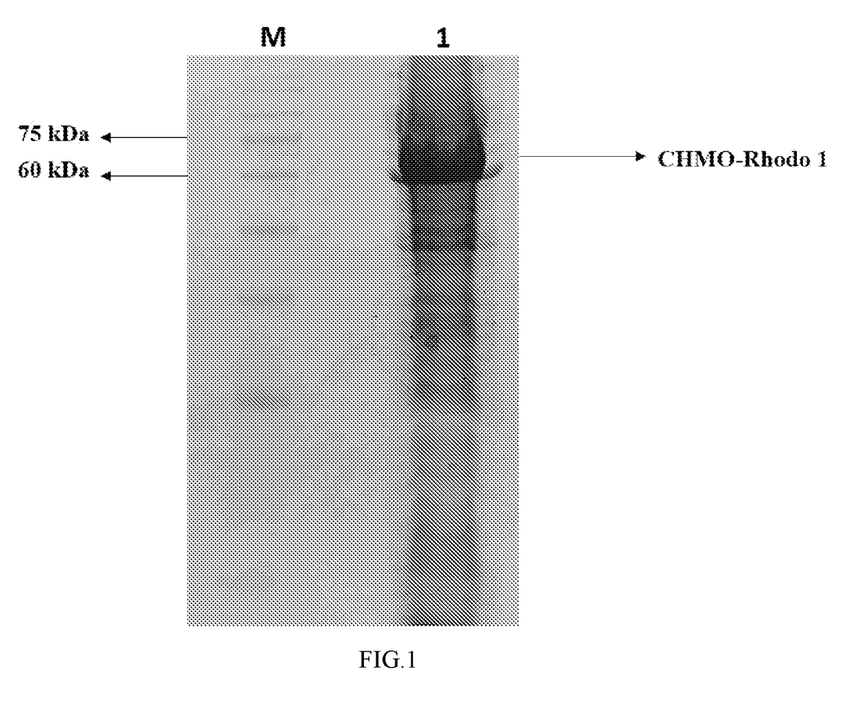
FIG. 1 is a SDS-PAGE electropherogram of a culture supernatant of a genetically-engineered bacterium expressing CHMO-Rhodo1, where M: marker; 1: the culture supernatant.
Figure 2:
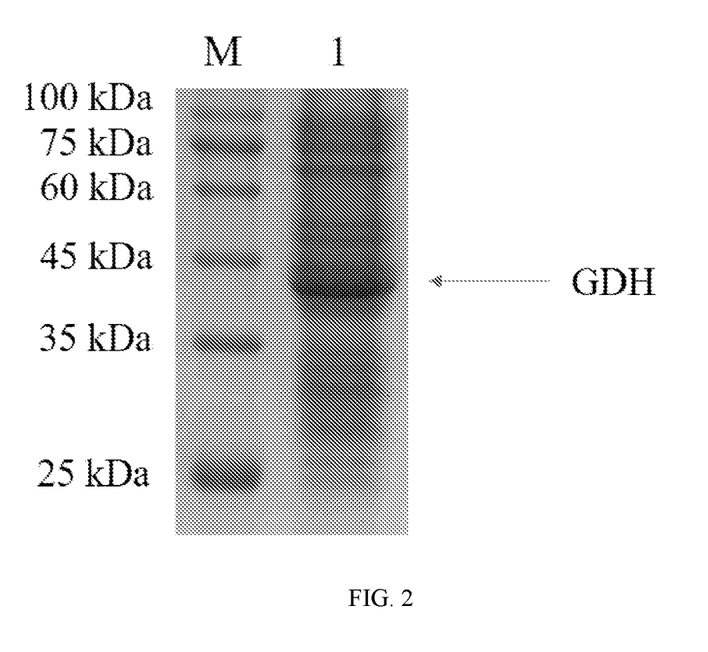
FIG. 2 is a SDS-PAGE electropherogram of a culture supernatant of a genetically-engineered bacterium expressing GDH, where M: marker; 1: the culture supernatant.

BL21(DE3)-CHMO-Rhodo1 monoclones were inoculated into 5 mL of a liquid LB medium with kanamycin resistance in a test tube and cultured in a shaker at 37° C. and 200 rpm for 8 h for activation. The activated culture was transferred to a liquid LB medium with kanamycin resistance in a volume ratio of 1:100 in a shake flask, and cultured at 37° C. under shaking at 200 rpm for 3 h. When the absorbance at 600 nm ($OD_{600}$) reached 1.2, isopropyl-thiogalactoside (IPTG) was added as an inducer to the bacterial suspension to a final concentration of 0.1 mmol/L. The induction was performed at 18° C. for 18 h, and then the bacterial suspension was centrifuged at 8,500 rpm for 10 min. The cells were collected and resuspended with a 250 mmol/L sodium phosphate buffered solution (pH 7.5) to obtain a suspension of resting cells containing the CHMO-Rhodo1 gene. The suspension of resting cells was ultrasonicated at 45% power for 30 min for disruption, and then centrifuged to obtain a supernatant containing the CHMO- Rhodo1 (referred to as the CHMO supernatant). An appropriate amount of the CHMO supernatant was taken and detected by sodium dodecyl sulfate-polyacrylamide gel electrophoresis (SDS-PAGE), and the results were shown in FIG. 1. The remaining CHMO supernatant was stored at 4° C. for use.

2. Construction of GDH Genetically-Engineered Bacteria and Induced Expression of GDH Gene (1) Preparation of GDH genetically-engineered bacteria The recombinant expression vector containing GDH gene and GDH genetically-engineered bacteria (named BL21 (DE3)-GDH) were prepared basically in accordance with the process mentioned above, and the difference was only that the CHMO gene was replaced with the GDH gene.

The sequence of the GDH gene was shown in SEQ ID NO:3, which was derived from *Thermoplasma acidophilum*, but was not limited thereto.

(2) Preparation of GDH-containing supernatant

BL21(DE3)-GDH monoclones were inoculated into 5 mL of a liquid LB medium with kanamycin resistance in a test tube and cultured in a shaker at 37° C. and 200 rpm for 8 h for activation. The activated culture was transferred to a liquid LB medium with kanamycin resistance in a volume ratio of 1:100 in a shake flask, and cultured at 37° C. under shaking at 200 rpm for 3 h. When the absorbance at 600 nm ($OD_{600}$) reached 0.8, IPTG was added as an inducer to the bacterial suspension to a final concentration of 0.1 mmol/L. The induction was performed at 18° C. for 16 h, and then the bacterial suspension was centrifuged at 8,500 rpm for 10 min. The cells were collected and resuspended with a 250 mmol/L sodium phosphate buffered solution (pH 7.5) to obtain a suspension of resting cells containing the GDH gene. The suspension of resting cells was ultrasonicated at a 45% power for 30 min for disruption, and then centrifuged to obtain a supernatant containing the GDH (referred to as the GDH supernatant). An appropriate amount of the GDH supernatant was taken and detected by sodium dodecyl sulfate-polyacrylamide gel electrophoresis (SDS-PAGE), and the results were shown in FIG. 1. The remaining GDH supernatant was stored at 4° C. for use.

Example 2 Reaction Monitoring

The CHMO supernatant and the GDH supernatant prepared in Example 1 were mixed, and then the mixed supernatant was added with a raceme of a substituted bicyclo[3.2.0]-hept-2-en-6-one, a solvent, a hydrogen donor and a cofactor, and mixed. The reaction mixture was subjected to asymmetric Baeyer-Villiger oxidation to produce a (1S,5R)-bicyclolactone, as shown in the following reaction scheme. The preparation process was specifically depicted in Examples 4-6.

The levels of the raceme of the substituted bicyclo [3.2.0]-hept-2-en-6-one (II) and the product (1S,5R)-bicyclolactone (I) were measured by gas chromatography (GC) during the asymmetric Baeyer-Villiger oxidation reaction to determine the conversion degree. 100 μL of the reaction mixture respectively collected at different time points was mixed with an equal volume of ethyl acetate, and centrifuged. An upper ethyl acetate layer was collected and filtered with a 0.3 M filter membrane, and the resulting filtrate was collected for GC analysis.

Figure 3:
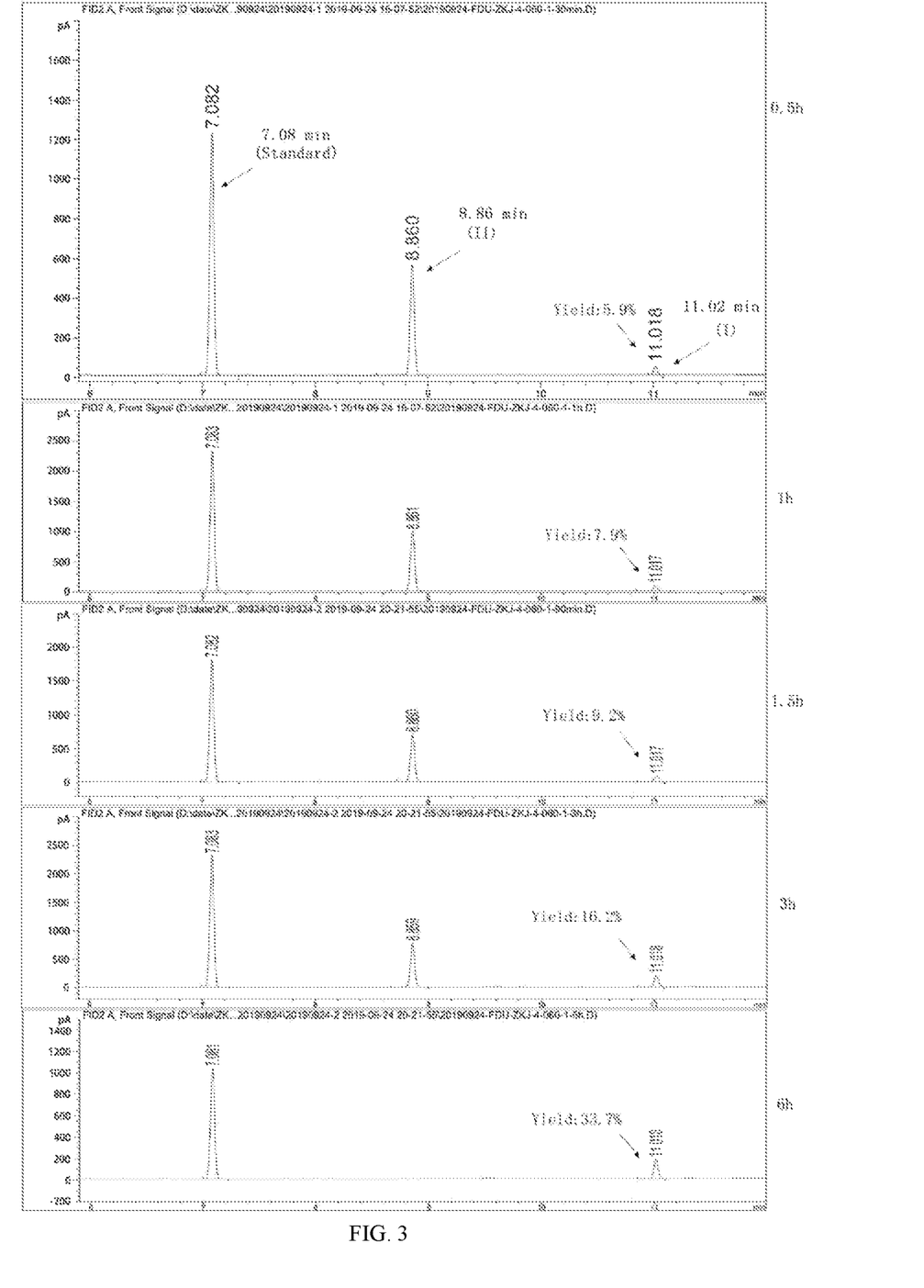
FIG. 3 is a series of gas chromatograms showing the levels of a raceme of a substituted bicyclo[3.2.0]-hept-2-en-6-one and the (1S,5R)-bicyclolactone at different time points during the reaction.
Figure 4:
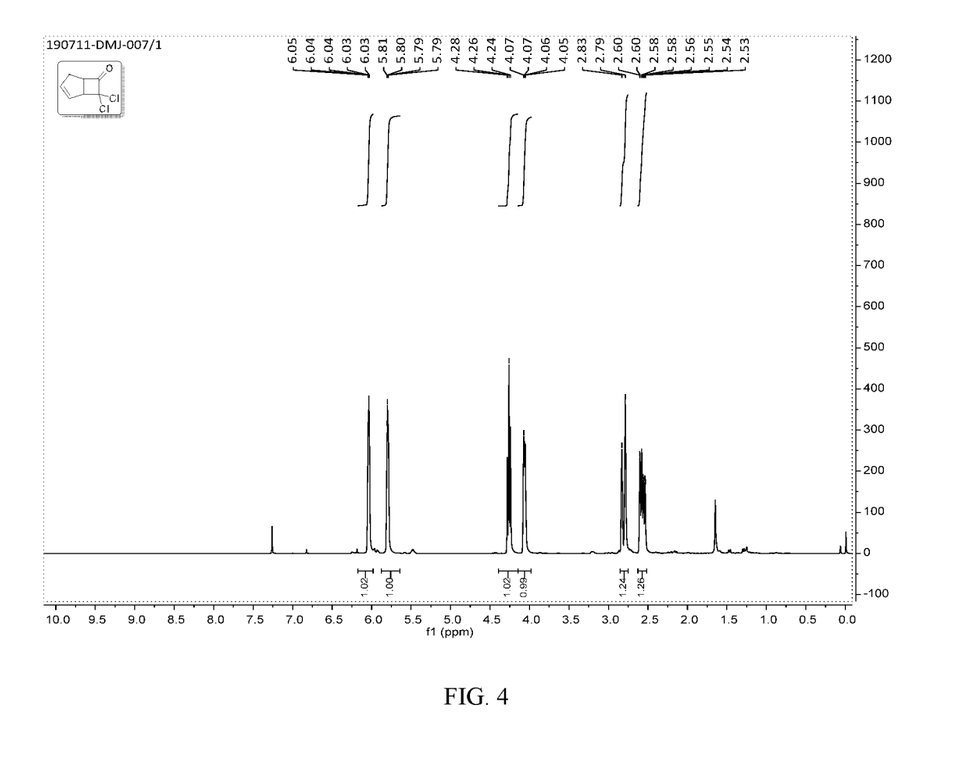
FIG. 4 is a $^1$H-NMR spectrum of a substrate 7,7-dichlorobicyclo[3.2.0]-hept-2-en-6-one.
Figure 5:
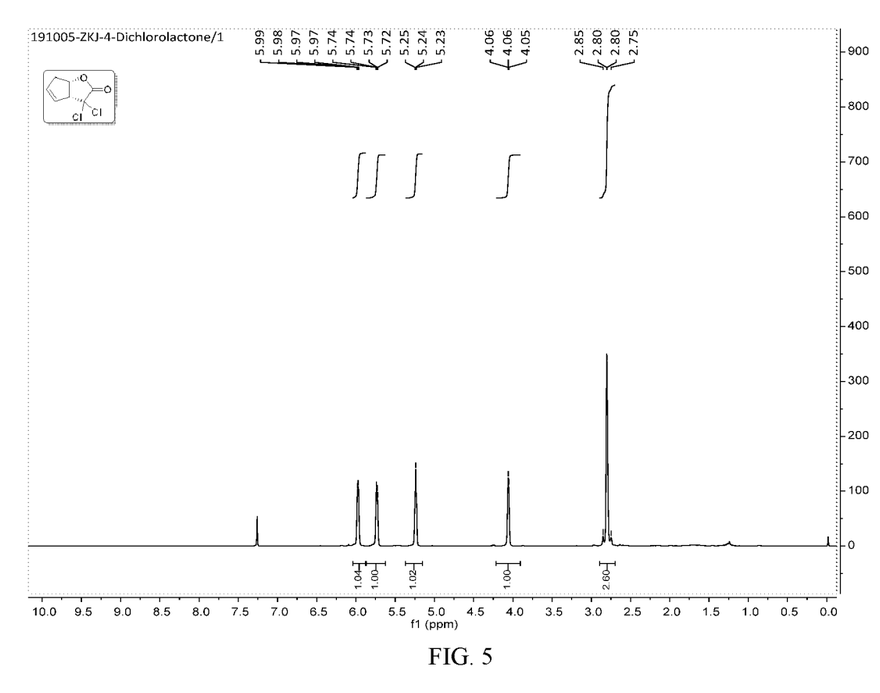
FIG. 5 is a $^1$H-NMR spectrum of the product (1S,5R)-7,7-dichlorobicyclic lactone.
Figure 6:
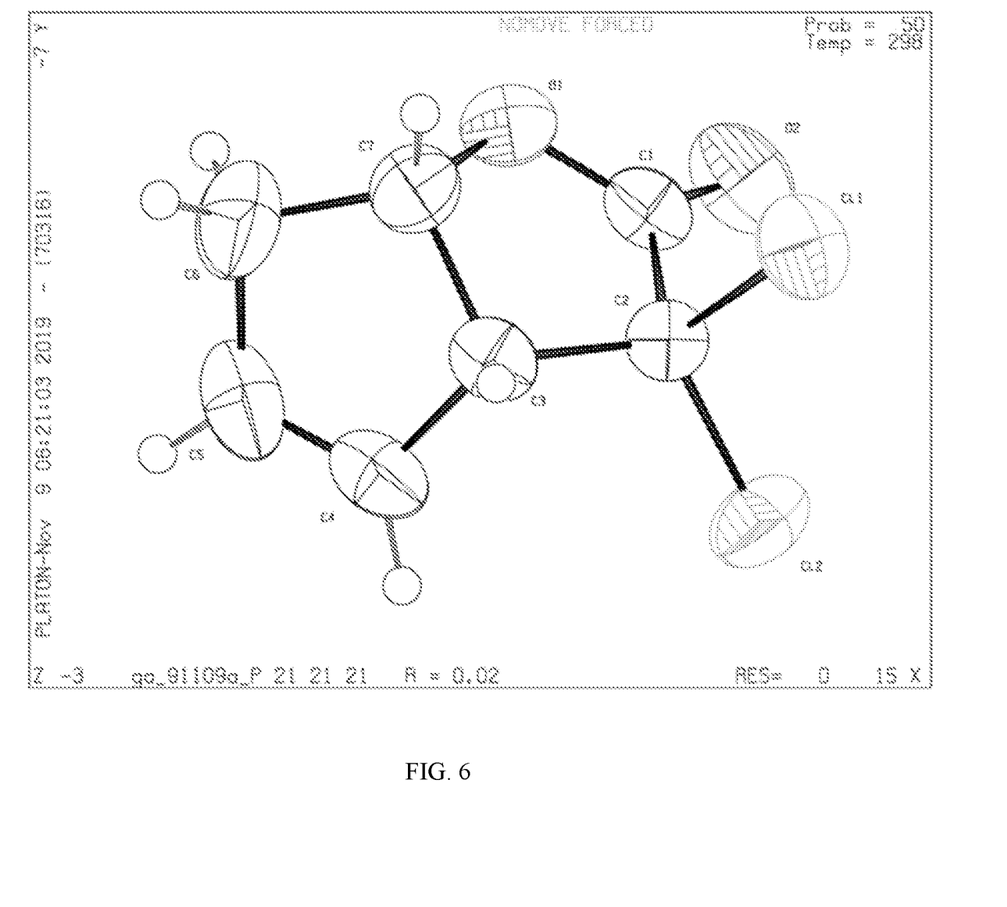
FIG. 6 is a single crystal XRD pattern of the product (1S,5R)-7,7-dichlorobicyclic lactone (CCDC: 1978566).

GC parameters: chromatographic column: Agilent DB-624 (0.32 mm×30 m); carrier gas: high-purity nitrogen; flow rate: 1.5 mL/min; detector: DAD; temperature: 250° C.; injection volume: 1 mL; split ratio: 20:1; temperature program: initial temperature: 80° C.; 80-130° C. at a rate of 10° C./min; 130-230° C. at a rate of 20° C./min; and 230° C. for 2 min. The GC monitoring results were shown in FIG. 3, where the raceme of the substituted bicyclo[3.2.0]-hept-2-en-6-one (II) had a retention time of 8.86 min, and its $^1$H-NMR spectrum was shown in FIG. 4; the product (1S,5R)-bicyclolactone (I) had a retention time of 11.02 min, and its $^1$H-NMR spectrum was shown in FIG. 5 and its absolute configuration was presented in the XRD single crystal pattern in FIG. 6.

Figure 7:
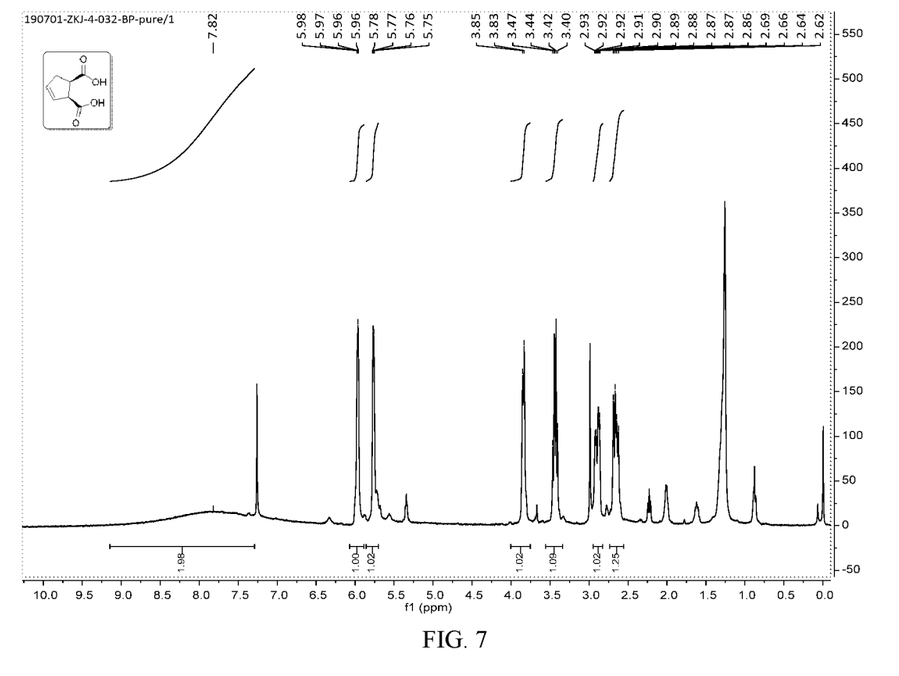
FIG. 7 is a $^1$H-NMR spectrum of product (1R,2S)-orthodicarboxy cyclopentene (IV).

The product (1R,2S)-dicarboxy cyclopentene (IV) was characterized by $^1$H-NMR, as shown in FIG. 7.

Example 3 Determination of ee of Target Product

The CHMO supernatant and the GDH supernatant prepared in Example 1 were mixed, and then the mixed supernatant was added with a raceme of a substituted bicyclo[3.2.0]-hept-2-en-6-one, a solvent, a hydrogen donor and a cofactor, and mixed. The reaction mixture was subjected to asymmetric Baeyer-Villiger oxidation to produce a (1S,5R)-bicyclolactone, as shown in the following reaction scheme. The preparation process was specifically depicted in Examples 4-6.

The ee of the target product (1S,5R)-bicyclolactone was determined by chiral supercritical fluid chromatography (SFC) under the following conditions: column: Chiralpak IF (4.6 mm×250 mm); mobile phase: $CO_2$/MeOH=95:5; flow rate: 3 mL/min; injection volume: 5 µL; detection wavelength: 220 nm. Before the SFC analysis, the target product (1S,5R)-bicyclolactone (I) was required to be dissolved with chromatographic grade anhydrous methanol.

Figure 8:
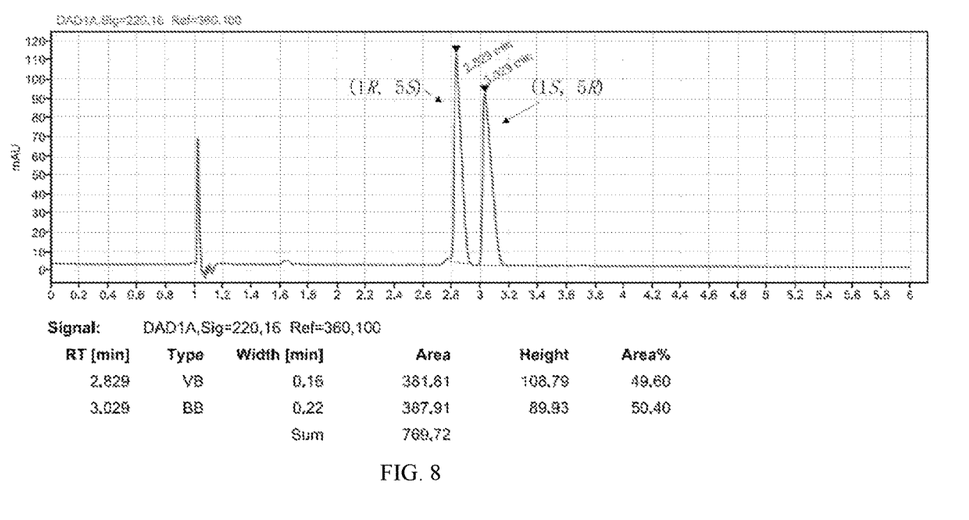
FIG. 8 is a HPLC map of Racemic-7,7-dichlorobicyclic lactone.

A HPLC map of the product Racemic-7,7-dichlorobicyclic lactone was shown in FIG. 8, from which it can be seen that retention times of (1R,5S)-7,7-dichlorobicyclic lactone and (1S,5R)-7,7-dichlorobicyclic lactone were 2.82 min and 3.029 min, respectively.

Figure 9:
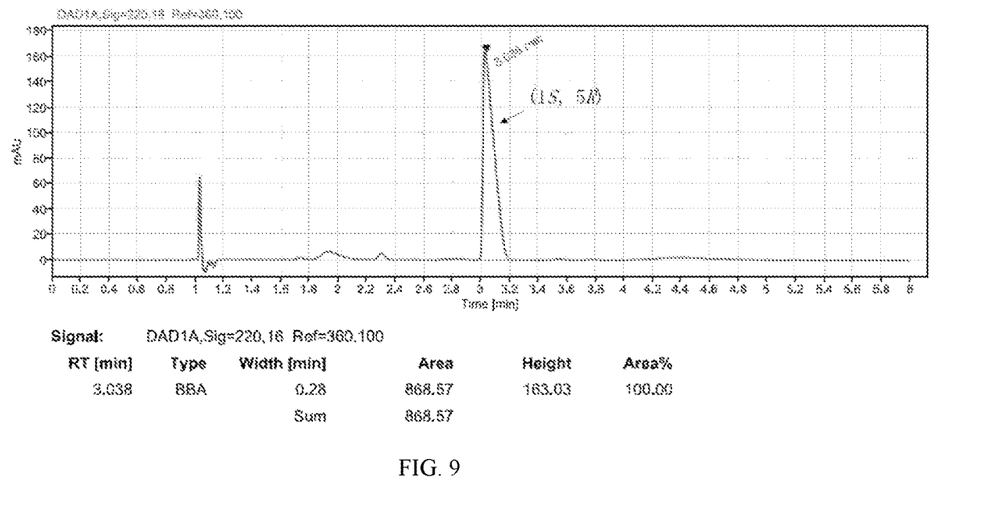
FIG. 9 is a HPLC map of (1S,5R)-7,7-dichlorobicyclic lactone.

A HPLC map of (1S,5R)-7,7-dichlorobicyclic lactone was shown in FIG. 9.

Example 4 Preparation of
(1S,5R)-7,7-dichlorobicyclic Lactone 42 mL (corresponding to 1.31 g (wet weight) of cells) of the CHMO supernatant and 12 mL (corresponding to 750 mg (wet weight) of cells) of the GDH supernatant prepared in Example 1 were mixed, and then the mixed supernatant was added with 0.6 mL of a solution of 1.0 M racemic-7,7-dichlorobicyclo[3.2.0]-hept-2-en-6-one (final concentration of 10 mM) in dimethyl sulfoxide (DMSO), 3.6 mmol of cosubstrate glucose (final concentration of 60 mM), $1.2 \times 10^{-5}$ mmol of NADP$^+$ (final concentration of 0.2 mM) and $3 \times 10^{-6}$ mmol of FAD (final concentration of 0.05 mM). The reaction mixture was diluted to 60 mL with 250 mM sodium phosphate buffered solution (pH 7.5), placed in a water bath at 25° C. and reacted under stirring for 1-2 hours. After the substrate was confirmed by GC to be completely consumed, the reaction mixture was subjected to extraction with an equal volume of ethyl acetate 3-4 times, and the organic phases were collected and combined. The combined organic phase was washed with saturated sodium bicarbonate solution 2 times, water once and saturated sodium chloride solution once, dried with anhydrous sodium sulfate and distilled under vacuum to remove the solvent to produce a target product (1S,5R)-7,7-dichlorobicyclic lactone (32% yield (determined by GC); 99% ee (measured by SFC)).

Example 5 Preparation of
(1S,5R)-7,7-dichlorobicyclic Lactone 25 mL (corresponding to 415 mg (wet weight) of cells) of the CHMO supernatant and 0.9 mL (corresponding to 15 mg (wet weight) of cells) of the GDH supernatant prepared in Example 1 were mixed, then the mixed supernatant was added with 0.6 mL of a solution of 0.5 M racemic-7,7-dichlorobicyclo[3.2.0]-hept-2-en-6-one (final concentration of 10 mM) in 1,2-dichloroethane (DCE) solution, 1 mL of toluene, 1.8 mmol of cosubstrate glucose (final concentration of 60 mM), $6 \times 10^{-6}$ mmol of NADP$^+$ (final concentration of 0.2 mM) and $1.5 \times 10^{-6}$ mmol of FAD (final concentration of 0.05 mM). The reaction mixture was diluted to 30 mL with 250 mM sodium phosphate buffered solution (pH 7.5), placed in a water bath at 25° C. and reacted under stirring for 5-7 hours. After the substrate was confirmed by GC to be completely consumed, the reaction mixture was subjected to extraction with an equal volume of ethyl acetate 3-4 times, and the organic phases were collected and combined. The combined organic phase was washed with saturated sodium bicarbonate solution 2 times, water once and saturated sodium chloride solution once, and dried with anhydrous sodium sulfate and distilled under vacuum to remove the solvent to produce a target product (1S,5R)-7,7-dichlorobicyclic lactone (34% yield (determined by GC); 99% ee (measured by SFC)).

Example 6 Preparation of
(1S,5R)-7,7-dichlorobicyclic Lactone 87 mL (corresponding to 290 mg (wet weight) of cells) of the CHMO supernatant and 3 mL (corresponding to 10 mg (wet weight) of cells) of the GDH supernatant prepared in Example 1 were mixed, then the mixed supernatant was added with 2 mL of a solution of 0.5 M racemic-7,7-dichlorobicyclo[3.2.0]-hept-2-en-6-one (final concentration of 10 mM) in dichloroethane (DCE) solution, 3.3 mL of toluene, 2 mmol of cosubstrate glucose (final concentration of 20 mM), $2 \times 10^{-5}$ mmol of NADP$^+$ (final concentration of 0.2 mM) and $5 \times 10^{-6}$ mmol of FAD (final concentration of 0.05 mM). The reaction mixture was diluted to 100 mL with 250 mM sodium phosphate buffered solution (pH 7.5), placed in a water bath at 25° C. and reacted under stirring for 5-7 hours. After the substrate was confirmed by GC to be completely consumed, the reaction mixture was subjected to extraction with an equal volume of ethyl acetate 3-4 times, and the organic phases were collected and combined. The combined organic phase was washed with a saturated sodium bicarbonate solution 2 times, water once and saturated sodium chloride solution once, dried with anhydrous sodium sulfate and distilled under vacuum to remove the solvent to produce a target product (1S,5R)-7,7-dichlorobicyclic lactone (30% yield (determined by GC); 99% ee (measured by SFC)).

It should be noted that the embodiments described above are merely illustrative of the invention, and are not intended to limit the invention. Any change, modification and replacement made by those skilled in the art without departing from the spirit of the invention should fall within the scope of the invention.

What is claimed is:

1. A method of synthesizing (1S,5R)-bicyclolactone, comprising:
   (1) constructing a first genetically-engineered bacterium containing a Baeyer-Villiger monooxygenase gene and a second genetically-engineered bacterium containing a glucose dehydrogenase gene;
   (2) preparing a first suspension of resting cells of the first genetically-engineered bacterium and a second suspension of resting cells of the second genetically-engineered bacterium;
   (3) preparing a first supernatant containing Baeyer-Villiger monooxygenase and a second supernatant containing glucose dehydrogenase; and
   (4) mixing the first supernatant and the second supernatant to obtain a mixed supernatant; mixing the mixed supernatant with a raceme of a substituted bicyclo [3.2.0]-hept-2-en-6-one, a solvent, a hydrogen donor and a cofactor for an asymmetric Baeyer-Villiger oxidation to produce the (1S,5R)-bicyclolactone;
   wherein the Baeyer-Villiger monooxygenase has the amino acid sequence as shown in SEQ ID NO:1, or an amino acid sequence having an identity of more than 90% to SEQ ID NO:1.

2. The method of claim 1, wherein the nucleotide sequence of the Baeyer-Villiger monooxygenase gene is shown in SEQ ID NO:2, and the nucleotide sequence of the glucose dehydrogenase gene is shown in SEQ ID NO:3.

3. The method of claim 1, wherein the first genetically-engineered bacterium and the second genetically-engineered bacterium are constructed from *Escherichia coli* BL21 (DE3) containing an expression vector pET-28a.

4. The method of claim 1, wherein the first suspension is prepared through steps of:

inoculating the first genetically-engineered bacterium to a first kanamycin-containing medium followed by activation on a shaker;

culturing the first genetically-engineered bacterium to an optical density $OD_{600}$ of 0.8-1.2, and adding a first inducer followed by continuous culture;

centrifuging a culture system of the first genetically-engineered bacterium, and collecting cells of the first genetically-engineered bacterium; and suspending the cells of the first genetically-engineered bacterium with a first buffered solution to prepare the first suspension; and the second suspension is prepared through steps of:

inoculating the second genetically-engineered bacterium to a second kanamycin-containing medium followed by activation on the shaker;

culturing the second genetically-engineered bacterium to an optical density $OD_{600}$ of 0.8-1.2, and adding a second inducer followed by continuous culture;

centrifuging a culture system of the second genetically-engineered bacterium, and collecting cells of the second genetically-engineered bacterium; and suspending the cells of the second genetically-engineered bacterium with a second buffered solution to prepare the second suspension.

5. The method of claim 4, wherein the first inducer and the second inducer are both 0.05-0.8 mM isopropylthiogalactoside (IPTG); after the first inducer is added, the culture is performed at 15-25° C. for 8-24 h; and after the second inducer is added, the culture is performed at 15-25° C. for 8-24 h.

6. The method of claim 4, wherein the first buffered solution and the second buffered solution are both a 30-300 mM sodium phosphate buffered solution.

7. The method of claim 1, wherein the first supernatant is prepared by sequentially ultrasonicating and centrifuging the first suspension; and the second supernatant is prepared by sequentially ultrasonicating and centrifuging the second suspension.

8. The method of claim 1, wherein in step (4), a volume ratio of the first supernatant to the second supernatant is 3.5-29:1.

9. The method of claim 8, wherein the volume ratio of the first supernatant to the second supernatant is 20-29:1.

10. The method of claim 1, wherein the asymmetric Baeyer-Villiger oxidation reaction mixture comprises 1.0-100 g/L of the raceme of the substituted bicyclo[3.2.0]-hept-2-en-6-one; 5-750 g/L of the hydrogen donor and 0-0.5 mM of the cofactor; a cell concentration of the first suspension is 0.1-25 g (wet weight)/L; and a cell concentration of the second suspension is 0.1-25 g (wet weight)/L.

11. The method of claim 1, wherein the hydrogen donor is glucose, and the cofactor is a combination of $NADP^+$/NADPH and $FADH_2$/FAD.

12. The method of claim 10, wherein the hydrogen donor is glucose, and the cofactor is a combination of $NADP^+$/NADPH and $FADH_2$/FAD.

13. The method of claim 1, wherein the asymmetric Baeyer-Villiger oxidation is performed at 20-40° C. and pH 6.0-8.0.

14. The method of claim 13, wherein the asymmetric Baeyer-Villiger oxidation is performed at 20-25° C. and pH 6.5-7.5.

15. The method of claim 1, wherein in the asymmetric Baeyer-Villiger oxidation, the solvent is selected from the group consisting of dimethyl sulfoxide, N,N-dimethylformamide, N,N-dimethyl acetamide, benzene, toluene, ethylbenzene, chlorobenzene, bromobenzene, n-hexane, cyclohexane, acetonitrile, ethyl acetate, dichloromethane, 1,2-dichloroethane, methanol, ethanol, isopropanol and a combination thereof.

16. The method of claim 1, wherein the solvent is a mixture of toluene, 1,2-dichloroethane and a phosphate buffered solution.

17. The method of claim 16, wherein in the solvent, a volume ratio of the toluene to the 1,2-dichloroethane to the phosphate buffered solution is 3:2:95.

18. The method of claim 16, wherein the phosphate buffered solution is a 100-250 mM phosphate buffered solution at pH 6.5-7.5.

19. The method of claim 1, further comprising:

after the asymmetric Baeyer-Villiger oxidation is completed, subjecting the reaction mixture to extraction with ethyl acetate, and collecting organic phases;

combining the organic phases;

washing the combined organic phase with a saturated sodium bicarbonate solution, water and a saturated sodium chloride solution in sequence; and drying the washed organic phase with anhydrous sodium sulfate followed by vacuum distillation to produce the (1S,5R)-bicyclolactone.

20. The method of claim 19, wherein the extraction is performed 3-4 times with an equal volume of ethyl acetate; and the washing is performed twice with the saturated sodium bicarbonate solution, once with water and once with the saturated sodium chloride solution.

* * * * *